US008352174B2

(12) United States Patent
Milstein et al.

(10) Patent No.: US 8,352,174 B2
(45) Date of Patent: Jan. 8, 2013

(54) TARGETED MARCHING

(75) Inventors: Ido Milstein, Ramat Gan (IL); Shmuel Akerman, Binyamina (IL); Gad Miller, Paris (FR)

(73) Assignee: Algotec Systems Ltd., RaAnana (IL)

( * ) Notice: Subject to any disclaimer, the term of this patent is extended or adjusted under 35 U.S.C. 154(b) by 1440 days.

(21) Appl. No.: 10/597,221

(22) PCT Filed: Dec. 26, 2004

(86) PCT No.: PCT/IL2004/001168
§ 371 (c)(1),
(2), (4) Date: Jul. 17, 2006

(87) PCT Pub. No.: WO2005/069228
PCT Pub. Date: Jul. 28, 2005

(65) Prior Publication Data

US 2008/0091340 A1 Apr. 17, 2008

Related U.S. Application Data

(60) Provisional application No. 60/536,661, filed on Jan. 15, 2004.

(51) Int. Cl.
*G01C 21/00* (2006.01)

(52) U.S. Cl. ........ 701/400; 701/410; 701/416; 701/436; 701/425

(58) Field of Classification Search ........................ None
See application file for complete search history.

(56) References Cited

U.S. PATENT DOCUMENTS

| | | | | |
|---|---|---|---|---|
| 5,394,325 | A * | 2/1995 | Schneider, Jr. | 702/18 |
| 5,752,217 | A * | 5/1998 | Ishizaki et al. | 701/201 |
| 5,878,368 | A * | 3/1999 | DeGraaf | 701/209 |
| 6,038,509 | A * | 3/2000 | Poppen et al. | 701/210 |
| 6,324,478 | B1 | 11/2001 | Popovici et al. | |
| 6,418,373 | B1 * | 7/2002 | Omi et al. | 701/209 |
| 6,470,266 | B1 * | 10/2002 | Ito et al. | 701/209 |

(Continued)

FOREIGN PATENT DOCUMENTS

WO WO 2004/086310 7/2004

(Continued)

OTHER PUBLICATIONS

Cohen et al. "Global Minimum for Active Contour Models: A Minimal Path Approach", International Journal of Computer Vision, 24(1): 57-78, 1997.

(Continued)

*Primary Examiner* — Khoi Tran
*Assistant Examiner* — Bhavesh V Amin

(57) ABSTRACT

A method of finding a path from a start point to a target point, in multi-dimensional space, including: (a) determining a plurality of points in a physical space, including a start point and an target point; (b) computing, using a cost function, for said points an accumulated path cost from the start point to a point; representing a minimal cost path from the start point to the point with respect to an optimization criteria; (c) computing for at least some of said points an estimated-cost-to-target from a point to the target point; and (d) after computing said costs, determining at least one of a minimal path or a minimal path cost of a path from the start point to the target point in the physical space, wherein the determination is based on said accumulated path costs, and is minimal with respect to the optimization criteria.

41 Claims, 8 Drawing Sheets

U.S. PATENT DOCUMENTS

| | | | |
|---|---|---|---|
| 6,496,188 B1 | 12/2002 | Deschamps et al. | |
| 6,604,005 B1 | 8/2003 | Dorst et al. | |
| 6,687,615 B1 * | 2/2004 | Krull et al. | 701/210 |
| 2002/0100009 A1 | 7/2002 | Xing et al. | |
| 2002/0136437 A1 | 9/2002 | Gerard et al. | |
| 2003/0031351 A1 | 2/2003 | Yim | |
| 2005/0110791 A1 | 5/2005 | Krishnamoorthy et al. | |
| 2005/0152588 A1 | 7/2005 | Yoshida et al. | |
| 2008/0132774 A1 | 6/2008 | Milstein et al. | |

FOREIGN PATENT DOCUMENTS

| | | |
|---|---|---|
| WO | WO 2005/069223 | 7/2005 |
| WO | WO 2005/069228 | 7/2005 |

OTHER PUBLICATIONS

Cormen et al. "Introduction to Algorithms", 2nd Edition, MIT Press, Chap.22: 540-549, 2001.

Deschamps et al. "Fast Extraction of Minimal Paths in 3D Images and Applications to Virtual Endoscopy", Medical Image Analysis, 5: 281-299, 2001.

Li et al. "Combining Front Propagation With Shape Knowledge for Accurate Curvilinear Modeling", Medical Image Computing and Computer-Assisted Intervention—MICCAI 2003, 2879: 66-74, 2003.

Livingstone et al. "Fast Marching and Fast Driving: Combining Off-Line Search and Reactive A.I.", 4th International Conference on Intelligent Games and Simulation (Game-On 2993), 4 P., 2003.

Maddah et al. "Efficient Center-Line Extraction for Quantification of Vessels in Confocal Microscopy Images", Medical Physics, 30(2): 204-211, 2003.

Melchior et al. "Consideration of Obstacle Danger Level in Path Planning Using A* and Fast-Marching Optimisation: Comparative Study", Signal Processing, 83(11): 2387-2396, 2003.

Sethian "A Fast Marching Level Set Method for Monotonically Advancing Fronts", Proc. Natl. Acad. Sci. USA, 93(4): 1591-1595, 1996.

Sethian "Evolution, Implementation, and Application of Level Set and Fast Marching Methods for Advancing Fronts", Journal of Computational Physics, 169(2): 503-555, 2001.

Sethian "Fast Marching Methods", SIAM Review, 41(2): 199-235, 1999.

Sethian "Level Set Methods and Fast Marching Methods. Evolving Interfaces in Computational Geometry, Fluid Mechanics, Computer Vision, and Materials Science", Cambridge University Press, p.1-33, 1999. http://math.berkeley.edu/sethian/Books/sethian_book.ps.

Wink et al. "3D MRA Coronary Axis Determination Using a Minimum Cost Path Approach", Magnetic Resonance in Medicine, 47(6): 1169-1175, 2002.

Communication Relating to the Results of the Partial international Search Dated Jun. 2, 2005 From the International Searching Authority Re.: Application No. PCT/IL2004/001169.

International Preliminary Report on Patentability Dated Jul. 27, 2006 From the International Bureau of WIPO Re.: Application No. PCT/IL2004/001168.

International Preliminary Report on Patentability Dated Jul. 27, 2009 From the International Bureau of WIPO Re.: Application No. PCT/IL2004/001169.

International Search Report and the Written Opinion Dated Nov. 9, 2005 From the International Searching Authority Re.: Application No. PCT/IL2004/001169.

International Search Report and the Written Opinion Dated May 10, 2005 From the International Searching Authority Re.: Application No. PCT/IL2004/001168.

Official Action Dated Oct. 7, 2011 From the US Patent and Trademark Office Re. U.S. Appl. No. 10/597,226.

Notice of Allowance Dated Mar. 23, 2012 From the US Patent and Trademark Office Re. U.S. Appl. No. 10/597,226.

Official Action Dated Aug. 11, 2011 From the US Patent and Trademark Office Re. U.S. Appl. No. 10/597,226.

Response Dated Sep. 12, 2011 to Official Action of Aug. 11, 2011 From the US Patent and Trademark Office Re. U.S. Appl. No. 10/597,226.

Communication Pursuant to Article 94(3) EPC Dated Jan. 5, 2012 From the European Patent Office Re. Application No. 04806699.7.

Communication Pursuant to Article 94(3) EPC Dated Jan. 5, 2012 From the European Patent Office Re. Application No. 04806700.3.

* cited by examiner

TARGETED MARCHING

RELATED APPLICATION

The present application is a U.S. National Phase of PCT Application No. PCT/IL2004/001168, filed on Dec. 26, 2004, which claims the benefit under 35 U.S.C 119(e) of U.S. Provisional Application 60/536,661 filed Jan. 15, 2004, the disclosure of which is incorporated herein by reference.

This application is also related to a PCT application No. PCT/IL2004/001169 entitled "Vessel Centerline Determination", filed on Dec. 26, 2004 the disclosure of which is incorporated herein by reference.

FIELD OF THE INVENTION

The present invention relates to path finding and/or to calculating path costs, for example in physical and in computer applications.

BACKGROUND OF THE INVENTION

Path planning or path finding methods are used in many applications, for instance, in robotics, computer games, graphics, vision and imaging. Various path planning or path finding methods have been reported in the art, in particular A*, and Fast-marching methods. Shortest path algorithms on graphs, for example Dijkstra's algorithm, are described in Cormen, Leiserson and Rivest, "Introduction to Algorithms", McGraw-Hill.

A* is described in N. Nilsson, "Problem-Solving Methods in Artificial Intelligence", McGraw-Hill, N.Y., 1971. Fast-marching methods are described in J. A. Sethian, "A fast marching level set method for monotonically advancing fronts", Nat. Acad. Sci. 93(4) (1996) 1591-1595; and in Sethian, "Fast marching methods", SIAM Rev. 41 (2) (1999) 199-235; and in http://math.berkeley.edu/~sethian, and in a book by Sethian "Level-sets method and Fast Marching Methods: Evolving Interfaces in Computational Geometry, Fluid Mechanics, Computer Vision and Material Sciences", Cambridge University Press, 1999. Path planning methods are describes in United States Patents: U.S. Pat. No. 6,324,478; U.S. Pat. No. 6,604,005 and U.S. Pat. No. 6,496,188.

A* and Fast-Marching are compared in P. Melchior et al. "Consideration of obstacle danger level in path planning using A* and Fast-Marching optimization: comparative study", Signal Processing, v. 83 n. 11 p. 2387-2396, November 2003; and in Livingstone et al. "Fast marching and fast driving: combining off-line search and reactive A.I.", 4th International Conference on Intelligent Games and Simulation (GAME-ON 2003), November 2003, UK. The paper by Melchior relates to a mobile robot application. The paper by Livingstone relates to a video game.

A* usually solves a continuous path problems by converting the problem to a discrete problem defined by a graph and then finding a solution on the graph. Fast-Marching solves continuous path problems by using grid based numerical approximations to the underlying problem.

Finding paths in 3D images using Fast Marching is described in T. Deschamps and L. D. Cohen "Fast Extraction of Minimal paths in 3D images and application to virtual endoscopy", Medical Image Analysis, Vol. 5, Issue 4, December 2001.

The disclosures of all of the above referenced patents and publications are incorporated herein by reference, in their entirety.

SUMMARY OF THE INVENTION

An aspect of some embodiments of the invention, relates to finding a path (path finding) from a start point to a target point in a continuous space, taking into account various constraints, and minimizing one or more cost function (cost criterion) of the path. In an exemplary embodiment of the invention, the path finding takes into account costs along the path, including a cost estimate of undecided parts of the path. In an exemplary embodiment of the invention, the resulting path is a smooth path. In an exemplary embodiment of the invention, the path is determined in a space of two or more dimensions, for example, three, four or more dimensions. In an exemplary embodiment of the invention, the actual path finding is performed on a discrete space, such that an approximation of an optimal or semi-optimal path in the original space is found. In an alternative embodiment, the path finding is carried out on a continuous space. In some embodiments, the continuous space is sampled as needed.

In exemplary embodiments of the invention, the method is carried out on a physical space or on a model of a physical space. While a physical space need not actually be tangible (e.g., an image space), a physical space has the property that certain functions such as cost, are defined for all points therein. A distance function can be defined as an integral over all points between two points and is therefore defined for all pairs of points. Optionally, a specific metric is defined for the space, for example, an Euclidian metric.

In an exemplary embodiment of the invention, the path finding method trades off computational requirements with path optimality. Thus, while the method may execute quickly, finding an optimal solution may not be guaranteed. In an exemplary embodiment of the invention, such a trade-off is achieved by using an estimate of future costs. In an exemplary embodiment of the invention, a trade-off is achieved by using a less accurate cost function if certain types of future cost estimations are used, for example, smooth and/or continuous estimation functions. In one example, the less accurate cost function takes into account fewer neighbors than used in more accurate cost function computations. Optionally, a determined path is smoothed or otherwise processed after it is found, or as it is found, optionally, in a manner independent of the underlying physical space and/or its properties. In an exemplary embodiment of the invention, the tradeoff still allows a path that is within 30%, 20%, 10%, 5%, 3%, 2% or better of the best path to be found. These values are averages, for example, on 100 randomly selected problem cases each. Intermediate average valued paths can be found as well.

In an exemplary embodiment of the invention, the path finding comprises approximating a boundary propagation in the original problem space and finding a path which follows the boundary propagation in a cost-efficient manner. Optionally, the approximation comprises one or both of sampling the continuous space and approximating an exact propagation function (e.g., by sampling).

In an exemplary embodiment of the invention, a minimum cost path between a starting point S and a target point T is found by calculating costs at several points between S and T. Optionally these points are arranged on a grid. In an exemplary embodiment of the invention, the cost calculation at each point takes into account (a) a local cost of the point; (b) an accumulated path cost along the path until the point; and (c) an estimated cost to target point T (or some other target). In an exemplary embodiment of the invention, the accumulated path cost at a point is calculated using the accumulated path costs at one or more neighbors (e.g., nearby points) of the point and the local cost at the point.

In an exemplary embodiment of the invention, the estimated cost to target is used to guide path finding towards the target.

In some embodiments of the invention, the path is not constrained to pass through grid points. The found path is optionally not a simple path interconnecting grid points by straight lines and is not in the form of a straight line. In an exemplary embodiment of the invention, when the optimal path is not a straight line from S to T, the path found has a lower cost than a corresponding "best" path which is constrained to pass only through grid points.

In an exemplary embodiment of the invention, accumulated path costs are computed from an Eikonal equation ||gradient(U(p))||=L(p), where p is a point, U(p) is an accumulated path cost function, L(p) is a local cost function, || || is a norm, and where the condition L(p)>0 holds. The above equation is known as Eikonal equation. The gradient may be approximated, for instance by using a finite difference approximation.

In some embodiments of the invention the accumulated path cost at the target point approximates the minimal accumulated path cost of a path from the start point to the target point in the physical space.

There is thus provided in accordance with an exemplary embodiment of the invention, a method of finding a path from a start point to a target point, in multi-dimensional space, comprising:

(a) determining a plurality of points in a physical space, including a start point and an target point;

(b) computing, using a cost function, for said points an accumulated path cost from the start point to a point; representing a minimal cost path from the start point to the point with respect to an optimization criteria;

(c) computing for at least some of said points an estimated-cost-to-target from a point to the target point; and (d) after computing said costs, determining at least one of a minimal path or a minimal path cost of a path from the start point to the target point in the physical space, wherein the determination is based on said accumulated path costs, and is minimal with respect to the optimization criteria. Optionally, determining a plurality of points comprises generating a discrete model of said physical world. Alternatively or additionally, the accumulated path cost at the target point approximates a minimal accumulated path cost of a path from the start point to the target point in the physical space. Alternatively or additionally, the minimal path determined is made of line segments and each line segment connects two of said points. Optionally, the minimal path cost has a lower or equal cost than any zigzag path from the start point to the target point, wherein the zigzag path connects a plurality of said points, only by straight line segments.

In an exemplary embodiment of the invention, the minimal path determined is a continuous smooth line.

In an exemplary embodiment of the invention, the method comprises repeatedly updating the accumulated path costs until a stopping criteria is satisfied.

In an exemplary embodiment of the invention, the method comprises selecting additional points based on said computed costs.

In an exemplary embodiment of the invention, the accumulated path cost of a point is a function of a local cost of the point and an accumulated path cost of at least one neighbor point of the point.

In an exemplary embodiment of the invention, computing said accumulated path cost comprises solving an Eikonal equation. Optionally, solving comprises employing a finite-difference approximation to an Eikonal equation. Alternatively or additionally, computing said accumulated path cost at a point p is carried out by solving an Eikonal equation ||gradient(U(p))||=L(p), where U(p) is an accumulated path cost function, L(p) is a local cost function, || || is a norm, and where the condition L(p)>0 holds.

In an exemplary embodiment of the invention, computing said accumulated path cost (u) at a point P, in a three dimensional grid, is carried out by solving the equation:

$$L^2=\max(u-U_{x-1,y,z},u-U_{x+1,y,z},0)^2+$$
$$\max(u-U_{x,y-1,z},u-U_{x,y+1,z},0)^2+$$
$$\max(u-U_{x,y,z-1},u-U_{x,y,z+1},0)^2+$$

where L is the local cost and the U's are accumulated path costs for neighbors of P.

In an exemplary embodiment of the invention, computing said accumulated path cost is carried out using cost calculations suitable for a fast marching method.

In an exemplary embodiment of the invention, the points are on a regular grid.

In an exemplary embodiment of the invention, the points are on an irregular grid.

In an exemplary embodiment of the invention, the method examines grid points in a particular order.

In an exemplary embodiment of the invention, neighbors of a point are one or more adjacent grid points to the point.

In an exemplary embodiment of the invention, the points are selected ad-hoc and not according to an a priori grid.

In an exemplary embodiment of the invention, the points are arranged as a graph.

In an exemplary embodiment of the invention, neighbors of a point are one or more grid points at a certain distance or at a certain radius from the point.

In an exemplary embodiment of the invention, determining a path is carried out by a gradient descent method applied on said points with calculated costs.

In an exemplary embodiment of the invention, said cost to target is intentionally underestimated.

In an exemplary embodiment of the invention, said cost to target is intentionally overestimated.

In an exemplary embodiment of the invention, said cost to target is based on a Euclidian distance to said target.

In an exemplary embodiment of the invention, a collection data structure is used for obtaining a point with the smallest cost, wherein adding or removing a value from the collection, and reordering the collection has a computational cost of order O(log M) or better, where M is the number of points in the collection.

In an exemplary embodiment of the invention, a heap-type data structure is used for obtaining a point with the smallest cost.

In an exemplary embodiment of the invention, points are categorized and points of different categories are processed differently.

In an exemplary embodiment of the invention, costs of at least one point are updated after an initial calculation.

In an exemplary embodiment of the invention, costs of no points are updated after an initial calculation.

In an exemplary embodiment of the invention, (c) is applied less often than (b).

In an exemplary embodiment of the invention, (c) causes delayed evaluation of less promising points. Optionally, said delayed evaluation causes a lack of evaluation of at least 40% of points on a grid including said plurality of points.

BRIEF DESCRIPTION OF THE FIGURES

Non-limiting embodiments of the invention will be described with reference to the following description of exemplary embodiments, in conjunction with the figures. The figures are generally not shown to scale and any sizes are only meant to be exemplary and not necessarily limiting. In the figures, identical structures, elements or parts that appear in more than one figure are preferably labeled with a same or similar number in all the figures in which they appear, in which.

DETAILED DESCRIPTION OF EXEMPLARY EMBODIMENTS

Overview

The invention, in some embodiments thereof, generally relates to finding a path from a start point to a target point, taking into account various constraints, and minimizing some objective function which defines the total cost of the path. In some embodiments of the invention, an optimal solution is not expected to be achieved. However, there may be a corresponding reduction in computational requirements.

Finding a minimum cost path has been employed in many applications, such as robotics, medical image processing, geographic information systems, and wire routing. For instance, path finding is carried out by a travel guidance system which computes the fastest route (path) from the present position S of a vehicle to a desired target destination T taking into account all alternative routes (paths) from S to T and various constraints, such as, traffic jams. The fastest route is found by minimizing the travel time (travel cost). In another, robotic navigation example, the cost can be distance and the goal is to find the shortest path.

For some problems, finding a minimum cost path can be obtained by a direct mathematical solution; however, for many problems an optimal solution is found by search, typically using various heuristic methods.

For clarity of presentation, a non-limiting example of path finding in a computer game world is described first. Then the application of the method to additional examples is described.

Computer Game Example

Figure 1:
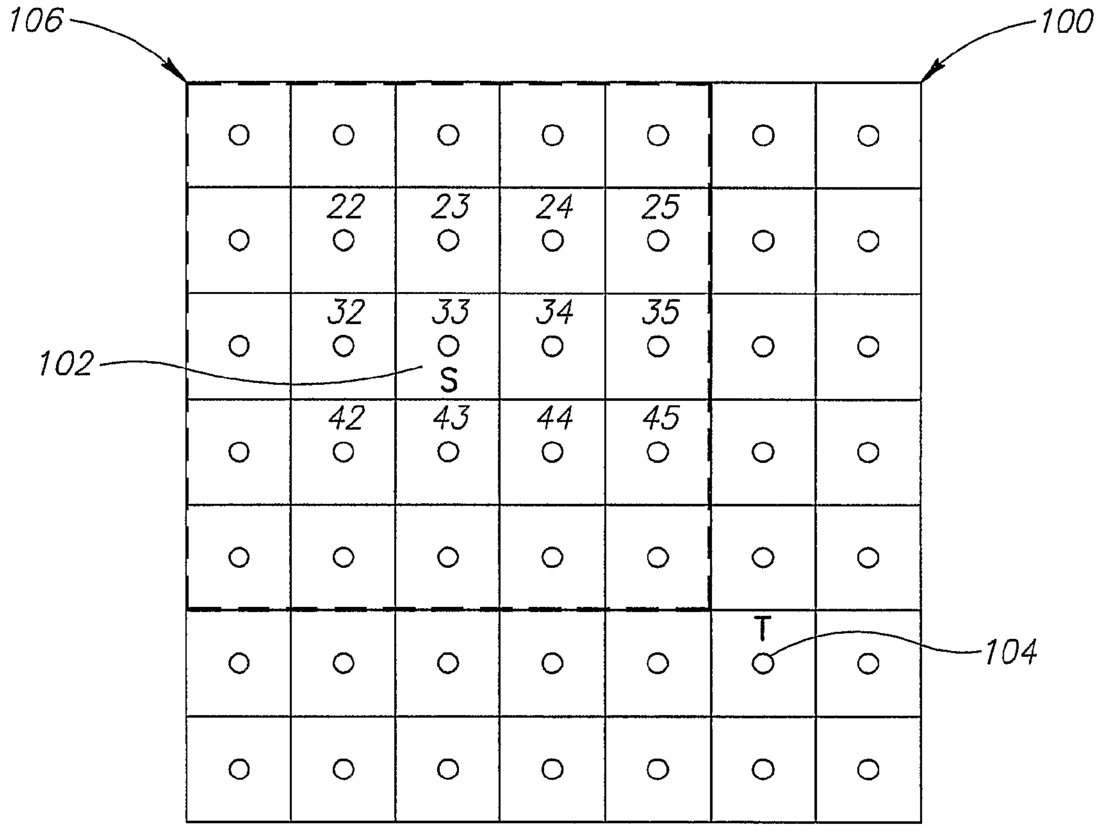
FIG. 1 shows a game grid example on which path finding is carried out, in accordance with an exemplary embodiment of the invention.

FIG. 1 shows a game grid 100 on which path finding is carried out, in accordance with an exemplary embodiment of the invention. The method finds a path from a start point S (102) to a target point T (104) which minimizes a total cost, for instance travel time. The path comprises a line that interconnects start 102 and target 104.

In general the path in a region is constrained by local and global constrains. One of the constraints optionally considered by the path finding method is a local cost, L, of a point in the region. The local cost of a point in the car game region depends on its degree of slowing down a car. Points with a higher local cost slow down a car more than points with lower local cost. For instance, a car can travel on a normal road (at cost 1), on a grass field (at cost 5), on a swamp (at cost 30); However true obstacles, such as rivers, can not be passed (cost infinite).

Grid 100 is a Cartesian grid formed of N×M cells which, for purpose of simplicity, is a uniform grid of equal size cells. Different points in the same cell have the same local cost (e.g. because they have the same terrain type). For simplicity the following description assumes only one point at each cell, which is the center of the cell. These points are also termed grid points (called also nodes or vertices) and are used by the method. However, it should be noted that a grid structure is used for simplicity or efficiency of calculation and is not strictly necessary for all embodiments of the invention.

It should further be noted that the grid structure is used to approximate the underlying world, however, the problem to be solved is finding a best path, even if it does not pass through centers of cells. In particular, as part of modeling the underlying physical world, a distance function (e.g., cost) is defined between any two points, not only centers of grids. In some embodiments of the invention, a cost at an arbitrary point is defined as a function of nearby points and the distances from those points, for example, a bi-linear approximation of costs at cell centers.

As a particular feature of some embodiments of the invention, the underlying physical world has a cost defined for each point therein, so that distances can be defined as integrals on the physical space. Thus, a minimal path can be defined in the physical world and which may not correspond to the grid. The grid is optionally used as an approximation method.

Path Finding Using Targeted Marching

The targeted marching method embodiment described is applied to a set of points $\{N_1, N_2 \ldots N_m\}$, which includes starting point S, and target point T and may be arranged in a grid. In some of the description below, the arrangement of the points in a grid will be assumed. However, this is not essential and other examples will be provided as well. The computation of the path is optionally based on costs associated with the points. As indicated above a path between S and T is chosen which minimizes (or comes close to minimizing) a total cost. The particular total cost criterion (total cost function) can depend on the optimization criteria used. For instance, in the game example, the optimization criterion is travel time.

In an exemplary embodiment of the invention, the method computes a total cost (TC) for the grid points, which is the sum of two costs: an accumulated path cost (G) and a cost to target (H).

The cost to target H (as used in the present embodiment) of a grid point P is an estimated cost from P to the target T. For instance, the length of the straight-line connecting P and T (or the cost of such a straight line) can be used to estimate H. In various embodiments of the invention, H is estimated in a manner which will usually provide an underestimation, or an over estimation. In some embodiments of the invention, H is estimated in a manner which does not generally guarantee an over estimation or an under estimation.

In an exemplary embodiment of the invention, the cost to target from a point is the Euclidian distance between the points multiplied by the lowest possible local cost. This ensures, in metric spaces where a triangular inequality exists, that the estimation is no more than the true cost (i.e. an under estimation).

In an exemplary embodiment of the invention, the cost to target can be estimated by: G (P)*dist (P to T)/dist(S to P); where G (P) is the accumulated path cost at point P, dist (P to T) is the Euclidian distance from point P to target T, and dist(S to P) is the Euclidian distance from starting point S to P.

In an exemplary embodiment of the invention, an accumulated path cost G is associated with grid point P. In some embodiments of the invention, the associated path cost is approximated, for example, from the path costs associated with neighboring points. In some embodiments of the invention it is ideal that accumulated path cost G is the minimum cost (e.g. travel times) of all paths from S to P; however, the actual calculation may be an approximation. In an exemplary embodiment of the invention, the accumulated path cost at point P is calculated using the accumulated path costs of the neighbors of P and the local cost at P. The minimum value of the new accumulated path cost calculated for P and the previous (e.g., stored) accumulated path cost at P will become the new accumulated path cost value associated with P. In an exemplary embodiment of the invention, at the initialization stage of the method, the accumulated path cost of starting point S is 0, and all other grid points have accumulated path cost of infinite.

Example of Path Cost Calculation for Game Example

The accumulated path cost (travel time) U[I,J] at point [I,J] of a grid can be calculated in various ways. A method of calculation which may be used is described in the Livingstone et al. reference cited above. Other exemplary methods are described below.

In the Livingstone et al. method, the minimum accumulated path costs Ux and Uy of neighboring nodes are:

$$U_x=\min(U_{i-1,j}, U_{i+1,j})$$

$$U_y=\min(U_{i,j-1}, U_{i,j+1})$$

The accumulated path cost U[I,J] is obtained from the quadratic equation $$(U_{i,j}-U_x)^2+(U_{i,j}-U_y)^2=(L)^2,$$

where L is the local cost at U[I,J].

The solution will be the minimum result that satisfies the condition:

$$U_{i,j}\geqq\max(U_{i-1,j}, U_{i+1,j}, U_{i,j-1}, U_{i,j+1}),$$

where the right hand terms are not of infinite value.

Grid Point Categorization

In an exemplary embodiment of the invention, grid points are categorized (tagged) by one of the following three tags: "trial", "alive" and "far". Optionally, this categorization is used for determining which grid points have already been visited such that their cost need not be computed. In this terminology, "alive" are points (nodes) already visited and at which the cost will generally not be changed; "trial" are points to be examined, and "far" are points not looked at yet. The different types of points ("trial" alive" and "far") may be processed differently, for example as described below. In an exemplary embodiment of the invention, initially the starting point is tagged as "trial" and all the other points are tagged as "far". Fewer or a greater number of tags may be used, in variations of the method.

Targeted Marching Demonstration

In an exemplary embodiment of the invention, the method examines grid points in a particular order. In some cases, this may increase the efficiency of the method. In an exemplary embodiment of the invention, cost calculation starts from the starting point S working outwards, i.e., looking at (nearest) neighbors of S, then at their (nearest) neighbors, and so on, until a stopping condition is met, for instance, until the target point T is reached.

Figure 2A:
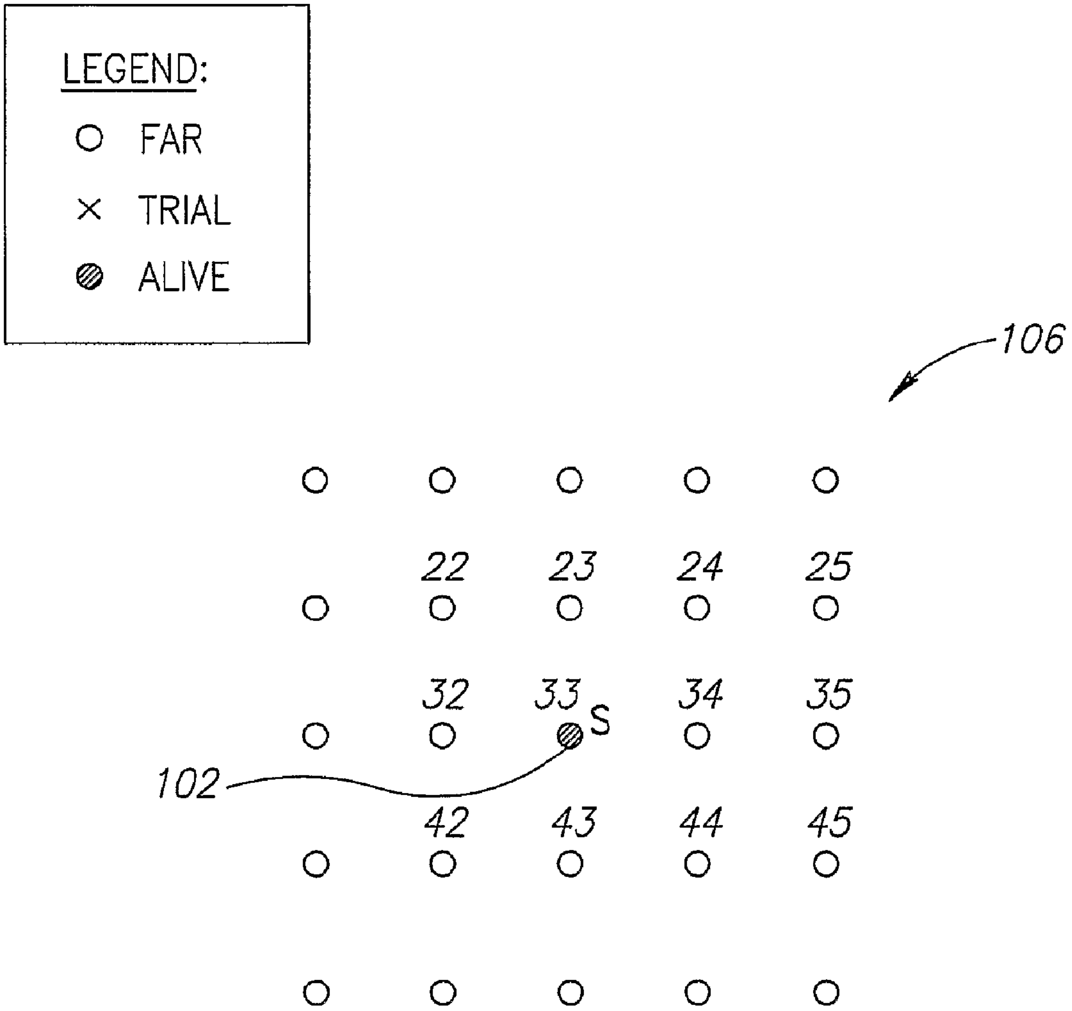
FIGS. 2A-2G illustrate a progression of tagging of points in a game grid example in accordance with an exemplary embodiment of the invention.
Figure 2B:
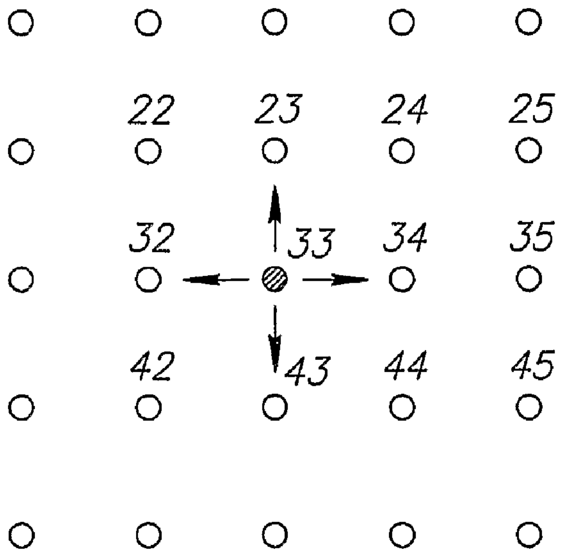

FIGS. 2A-2G illustrate a progression of tagging of points in the game grid example of FIG. 1, in accordance with an exemplary embodiment of the invention. The grid (106) of FIG. 2A is the upper left 5 rows by 5 columns grid (106) in FIG. 1, marked in FIG. 1 with a dashed line. In FIGS. 2A-2G, "far" points are denoted by hollow circles, "trial" points are marked with a cross sign, and "alive" grid points are solid circles. Each point is referred to in the following description by a two digit number in which the left digit indicates a row coordinate and the right digit indicate a column coordinate.

Figure 2C:
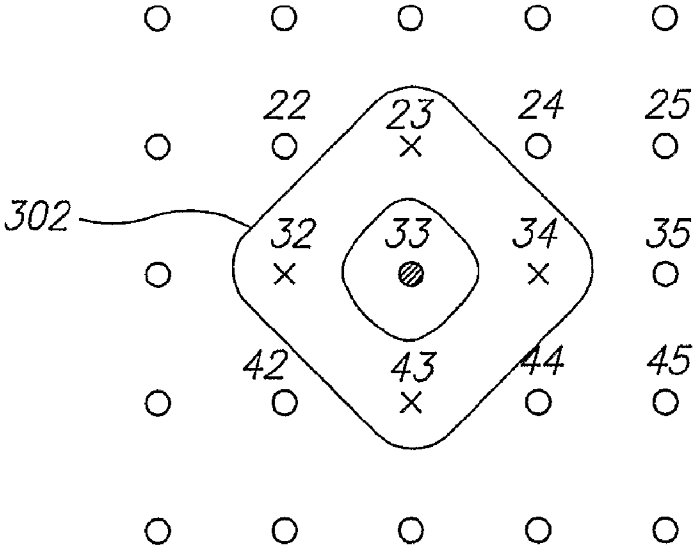
Figure 2D:
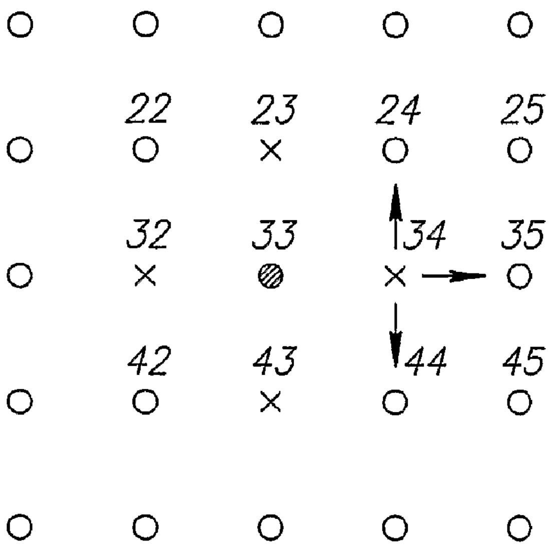
Figure 2E:
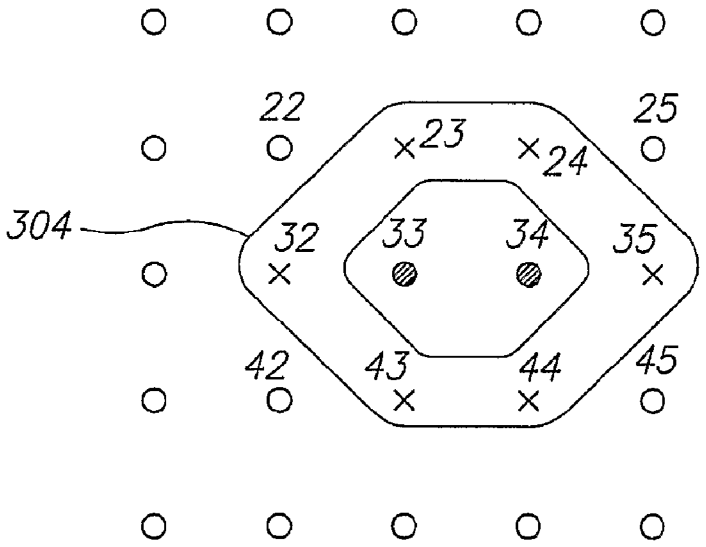
Figure 2F:
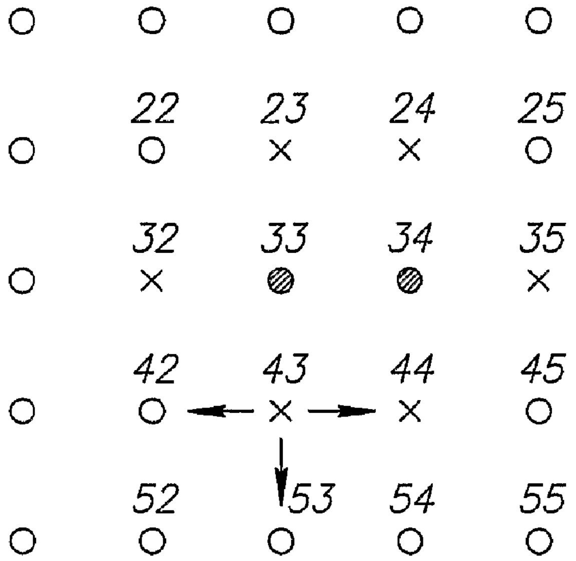
Figure 2G:
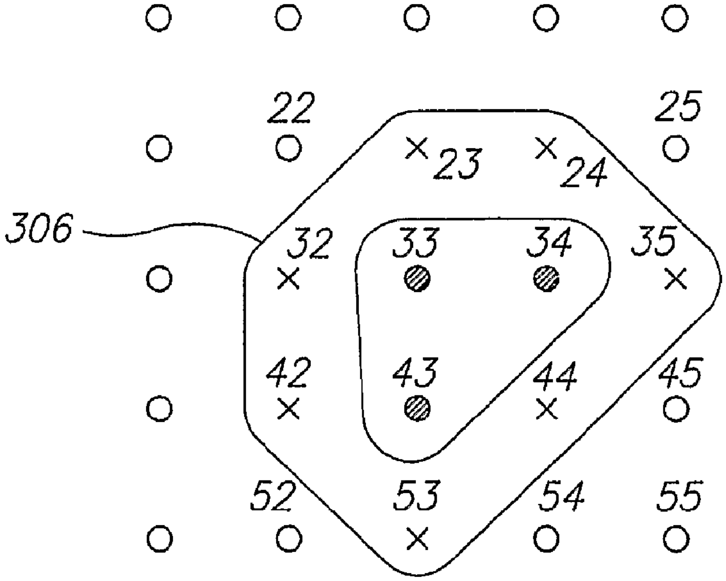
Figure 3A:
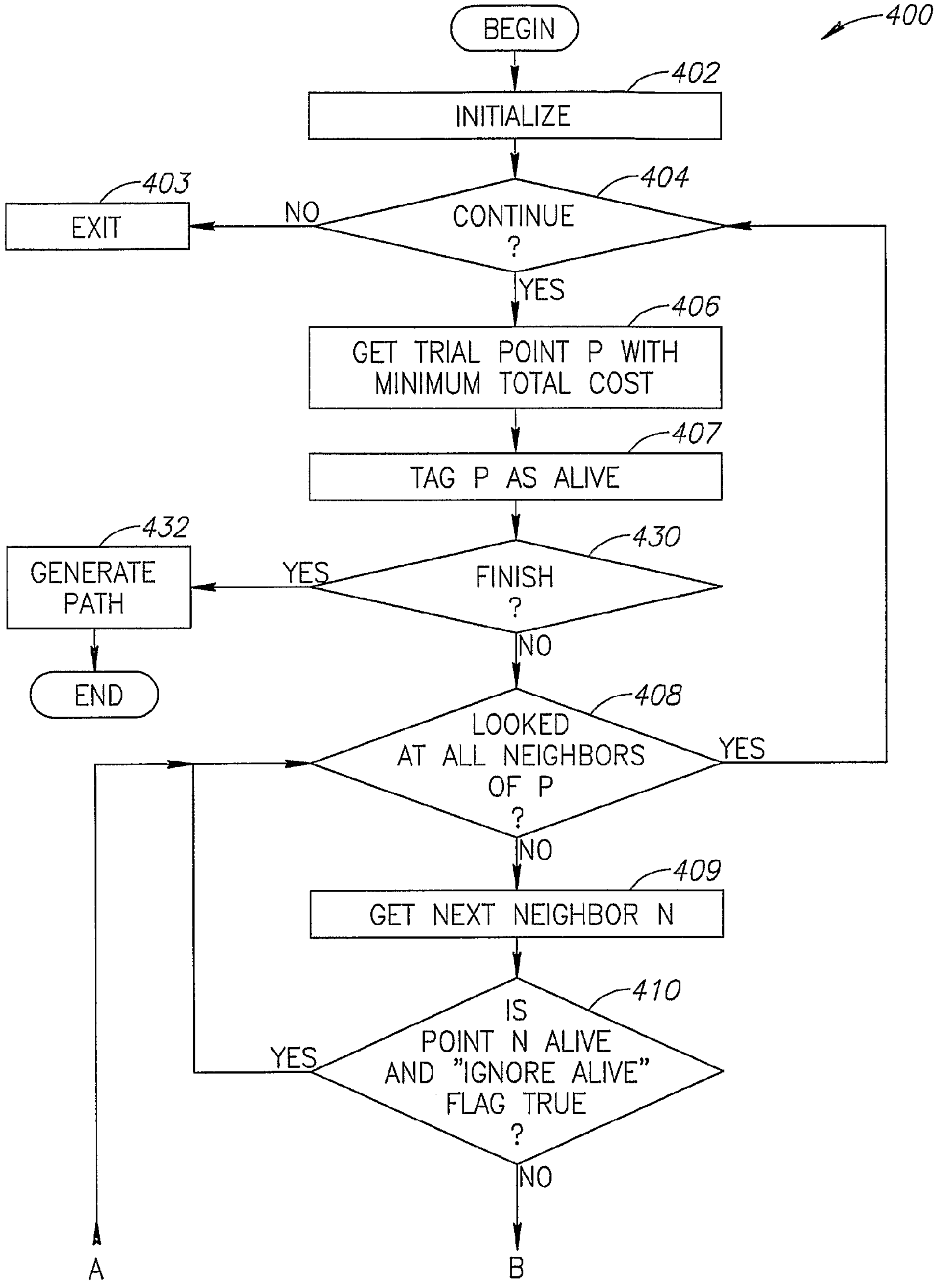
FIG. 3A-3B is a flowchart of a method of targeted marching, in accordance with an exemplary embodiment of the invention.
Figure 3B:
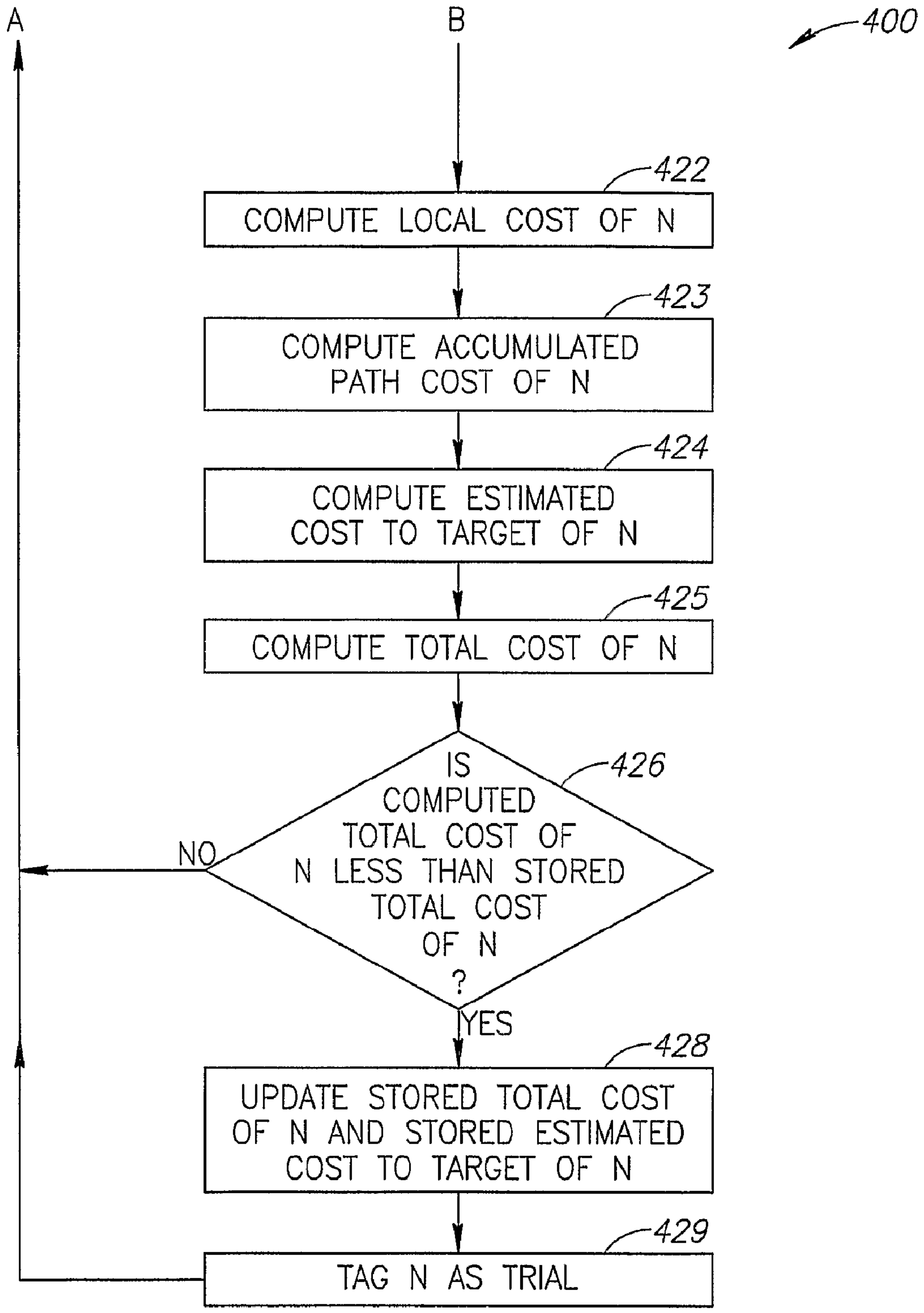

FIGS. 3A-3B, which will be described in greater detail below, is a flowchart of a targeted marching method, in accordance with an exemplary embodiment of the invention. In general, in FIGS. 2A-2G, the process of tagging proceeds as follows: a trial point is selected and cost calculations are carried out on at least some of the neighbors of the selected point. Then the process is repeated.

Initially, the starting point S (102) at a coordinate 33 is categorized as "trial". The other grid points are categorized as "far". From all the trial points a trial point having a lowest total cost, i.e. starting point 33, is chosen. Point 33 is tagged as "alive" (FIG. 2A), and the nearest neighbors of S are examined (FIG. 2B) for calculation of costs thereof. Points 23, 32, 34, and 43 are the nearest non alive neighbors of point 33 and costs are calculated for them. The points 23, 32, 34, and 43 that were "far" are tagged "trial" (FIG. 2C).

Now the process is repeated. From all the trial points a trial point which has the lowest total cost (point 34, for example) is chosen. The chosen point is usually a point in the direction of T. Of the neighbors (FIG. 2D) of point 34, points 24, 35, and 44 are not alive, a cost is calculated for them and they are tagged as "trial". Point 33 is already alive and is not considered or retagged (FIG. 2E) Point 34 is tagged as alive. Multiple lowest cost points may be processed in parallel. Optionally at least one of the points chosen is not a lowest cost point.

Again the process is repeated. A trial point which has the lowest total cost (for example, point 43) is selected. The nearest neighbors of 43, which are not alive (i.e., points 42, 44, and 53) are considered (FIG. 2F). Points 42 and 53 which were "far" are tagged as "trial". Point 44 was already tagged as "trial". The costs of points 42, 44, and 53 are updated, and point 43 is tagged as "alive" (FIG. 2G). This process may now be repeated until a stopping condition is met. Various stopping conditions may be used, for instance that the target node T has been reached or that too much time has passed.

In the above example (FIG. 2) costs are computed at the nearest non alive neighbors; However, in some embodiment of the method costs are computed also at the nearest alive neighbors, and those "alive" points, which get a lower cost than they had before, are tagged as "trial". In some embodiments of the invention, a cost of a point changes when a lower cost path to that point is found.

Targeted Marching Flowchart

FIGS. 3A-3B is a flowchart 400 of a method of targeted marching to determine a path, in accordance with an exemplary embodiment of the invention, which also incorporated the acts described in FIGS. 2A-2G.

In the game example, initially (at 402), the starting point S is categorized as "trial" and a total cost, usually zero, is associated with point S. The other entire grid points are categorized as "far" and are considered to have an associated total cost of infinite.

Calculating the costs of the grid points is carried out until a stopping condition (at 404 or at 430) is met. At 404 it is decided if to exit (act 403) or to continue (act 406). For example, it will be decided to exit if there are no more trial points. At 430 it is decided to finish if the target point is tagged as "alive". A path is optionally generated at 432, as will be described below. Optionally, no path is generated. Instead, the result can be a cost of a low cost path.

At 406, a point P with a minimum total cost is chosen from the trial points. In the game example the first chosen point P will be the starting point S.

At 407 point P is tagged as "alive".

The condition at 408 is used to control a loop of looking at all neighbors of P.

At 409, a neighbor N of P is obtained. After all neighbors of P have been looked at (act 408) the method continues at 404. In some cases, a neighbor point N that is alive is ignored. This is carried out at 410. The method uses a flag "IGNORE ALIVE". If at 410 point N is alive and the "IGNORE ALIVE" flag is TRUE, point N is ignored and the method continues at 408; otherwise the method continues at 422.

In an exemplary embodiment of the invention, the flag "IGNORE ALIVE" is set to be "true" in the case where the estimated cost to target is a continuous and optionally smooth function. Alternatively in some embodiments of the method "IGNORE ALIVE" is set to "false", trading off more computation time with possibly finding a lower cost path. If "IGNORE ALIVE" is set to false and the cost to target estimation is an underestimation the path found by the embodiment can be a path that has a lower or equal accumulated path cost than any other path computed by the embodiment. The path found can thus approximate the lowest path cost of all possible paths in the underlying physical problem. In the car example, it approximates the lowest travel time path in the real game world. It should be noted that the path found (e.g., as described below) does not necessarily pass through the grid points, except through the starting point and through the target point.

At 422, a local cost of neighbor point N is calculated or obtained. At 423, the local cost is used to calculate an accumulated path cost. At 424, cost to the target is estimated. At 425, the accumulated path cost and the cost to target are added together to give the total cost of the point N.

At 426 it is checked whether the new total cost of N is smaller than the previous total cost of N. In the case, no previous total cost of N exists or N is "far", it is assumed that the condition at 426 is true and the method continues to act 428.

The total cost of N obtained at 425 is stored at 428. The estimated cost to the target of N obtained at 424 is also stored at 428. While the description (act 428) suggests storing the total cost and the estimated cost to target, alternatively the accumulated path cost and cost to target may be stored for each point and the total cost computed from them. Since total cost=accumulated path cost+estimated cost to target, any 2 of the 3 items in the equation may be stored and the third item calculated from the other two.

Point N is tagged "trial" at 429. Notice that an "alive" point is tagged (at 429) "trial" only if its new total cost is less than its previous total cost (act 426). That is always the case for "far" points.

Including an estimation of the cost to target in the total cost may allow the method to converge faster, by ignoring paths that appear to be unsuitable based on their expected future costs. In some embodiments of the invention, estimated cost to target may be performed every few computation cycles.

One example of accumulated path cost calculation (at 423) was given above. In an exemplary embodiment of the invention, a method of calculation of accumulated path cost that is known for fast marching is also used for targeted marching. For instance, in a three dimensional grid, by solving the following equation for "u" (the accumulated path cost):

$$L^2=\max(u-U_{x-1,y,z},u-U_{x+1,y,z},0)^2+$$

$$\max(u-U_{x,y-1,z},u-U_{x,y+1,z},0)^2+$$

$$\max(u-U_{x,y,z-1},u-U_{x,y,z+1},0)^2+$$

in which L is the local cost and the U's are accumulated path costs for neighbors of P. One way to solve the above equation is by disregarding the "0" terms in the equation, and solving the resulted quadratic equation for "u". In some cases a solution to the quadratic equation is not possible. A best fit may be searched for. Alternatively, one or more of the "max" units may be replaced by zero. In an exemplary embodiment of the invention, a "max" unit to be replaced by zero is selected in the following manner. For each "max" unit, the smaller U value is found. Then, the "max" unit for which the smaller U value is largest is selected for removal. Points, which are not "alive", are optionally assumed to have infinite cost.

In an exemplary embodiment of the invention, accumulated path cost at a point is calculated using the accumulated path costs of (at least some of) the neighbors and the local cost at the point. Alternatively to the formula shown above, a different interpolation may be used, for example, an interpolation that is skewed in one direction (taking, for example, information from left points into greater consideration than points on the right, and/or talking into greater consideration points in a direction to a target or a direction from a target). In addition, the interpolation may be of a greater order and/or using a larger neighborhood, such as two neighbors away. Optionally, some of the neighbors are ignored.

The equation above is a discretization of an Eikonal equation $\|\text{gradient}(U(p))\|=L(p)$ on a Cartesian grid, where p is a point, U(p) is an accumulated path cost function, L(p) is a local cost function, $\|\,\|$ is an Euclidian norm, and where $L(p)>0$ holds.

The gradient in an Eikonal equation may be approximated in many different ways; one of them, for three dimensional grids, was given above.

It should be appreciated that other approximation methods are also within the scope of the invention. In general, a better approximation will yield lower cost paths. However, a faster approximation may result in faster path finding. In an exemplary embodiment of the invention, however, the approximated function is the underlying cost in the physical world. In some cases, a less precise equation may be approximated. For example, the approximation can be selected to have an accuracy of better than 5%, 3%, 1% or better, or intermediate values.

It should be noted that even if a lower path cost cannot be found using a different (e.g., better) approximation, a potential advantage of a better approximation is that the approximated path cost can be more trusted to accurately approximate a true cost of the path. This may prevent the selection of a non-optimal path due to calculation errors.

Referring to 406, selecting a trial point may be implemented using various data structures. In an exemplary embodiment of the invention, an efficient data collection structure termed herein "min-heap", is used. Points and optionally associated information, such as, cost and point category are stored in a min-heap. The "min-heap" allows obtaining, optionally very efficiently, the point (node) with the smallest (possibly equal) cost. The "min-heap" can be for instance a priority queue. A priority queue is a data structure that is designed to allow efficient removal of the highest priority item and in our case the item with minimum cost. The "min-heap" may be implemented, for instance, as a heap data structure. A heap is usually an efficient implementation of a priority queue and is usually implemented as a tree data structure. Even though a heap is not usually completely sorted, it has one very useful characteristic: the node with the highest priority will always be at the top of the tree. Adding or removing a point to/from a heap generally has a computational cost of the order O(log N), where N is the number of heap elements (items stored in the heap). One description of heap and heap maintenance may be found in Aho et al., the Design and Analysis of Computer Algorithms, Addison-Wesley 1974, pages 87-92, the disclosure of which is incorporated herein by reference.

Path Generation

After the costs of the grid points have been calculated, a path which minimizes the accumulated path cost can be determined or generated (at 432). Various approximation methods and/or numerical analysis methods can be used. One way to generate the path is by back-propagation from the target point T to the starting point S. The path will start at T and travel to a neighbor point P with lowest total cost, then to a neighbor N of P with lowest total cost and so on until S is reached.

In some embodiments of the invention, a gradient descent method or a Runge Kutta method is used to find a path. Thus, the found path need not pass through grid points. Whether or not the path passes through grid points, however, in an exemplary embodiment of the invention, the path approximates a best path in the underlying physical world, which is typically continuous.

The resulting path may be a zigzag line interconnecting grid points (e.g., if a method other than gradient descent is used). Optionally, the interconnecting lines are not limited to be straight and may be curved. In this and other cases, the resulting path is optionally post processed. For example, post processing can be used to smooth a path. Alternatively or additionally, numerical optimization techniques may be used to optimize a zigzag path, optionally taking into account costs defined for points not on the zig-zag path.

It should be noted that in some cases the correct (e.g., "best") solution is not smooth, however, smoothing may be practiced for various reasons. Also, the path generation function may also include a limitation on the curvature of the path.

It should be noted that the A* method cited above does not relate to the underlying physical world. Rather, a best path is found between graph nodes (point). For example, if a graph of a car game world is defined as a Cartesian grid, the alignment of the grid with the start and end points will determine the length of the best path. In a case where the grid is aligned with a straight line connecting to points, the length of the path will be the number of grid cells along the line. In a case where the grid is at 45 degrees rotation to the path, the length will be about 1.4 times greater.

The targeted marching method embodiment described can be visualized as working by expanding a wave-front. The wave-front contains all the trial points and models the expansion of the wave-front in an underlying physical world.

In FIG. 2A, initially the wave-front is at given point 33 and over time, the wave-front expands. In FIG. 2C, it expands from 33 to 23, 32, 34, and 43 (302 in FIG. 2C); then to 23, 24, 32, 35, 43, and 44 (304 in FIG. 2E); and then to 23, 24, 32, 35, 42, 44, and 53 (306 in FIG. 2G).

Figure 4A:
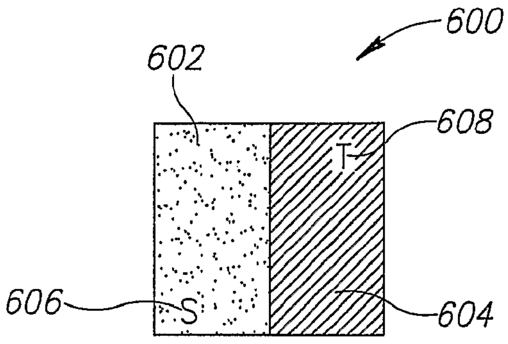
FIGS. 4A-4C illustrate path generation in a game grid example in accordance with an exemplary embodiment of the invention.
Figure 4B:
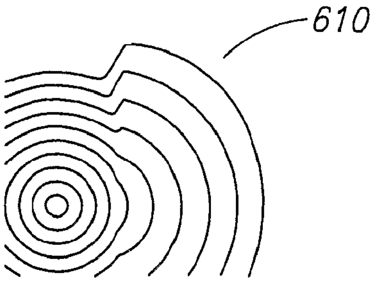
Figure 4C:
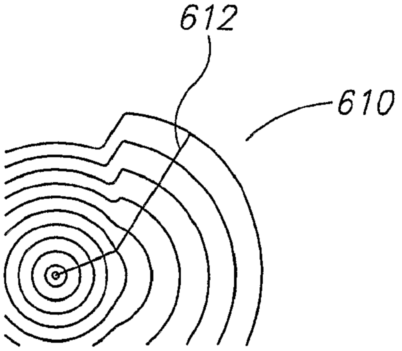

FIGS. 4A-4C illustrate path generation in a game grid example using gradient descent, in accordance with an exemplary embodiment of the invention. In FIG. 4A, the left half (602) of the region (600) is full of snow, and driving through snow is slower (FIG. 4A). The right half (604) of the region (600) is dry. In this case the path, from S (606) to T (608), which takes the least time, is not a straight line and not a line that zigzags between grid points. The method expands a (wave) front from S to T (610 in FIGS. 4B-4C). The minimum cost path can be generated tracing backwards from T to S always going perpendicular to the front (612 in FIG. 4C). As can be seen, the path generated and the propagation of the wave-front are not strictly limited to grid points.

Optionally, no path is generated. Instead, the result can be a cost of a low cost path. This may be useful, for instance, when multiple targets exist and it is desired to determine if a path to any of the targets, that has a cost lower than a given number, exists.

Variations

Several exemplary variations regarding grid points are described. In an exemplary embodiment of the invention, using more grid points in the same physical area, for instance, by using a shorter spacing between grid points, may produce a lower cost path and/or may increase the accuracy of calculating path costs.

Figure 5:
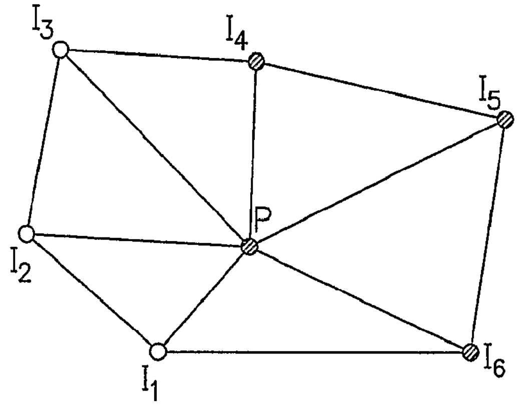
FIG. 5 illustrates a point and its neighbors in accordance with an exemplary embodiment of the invention.

In an exemplary embodiment of the invention, the points considered by the method do not have to be on a regular grid. FIG. 5 illustrates a point P and its neighbor's I1, I2, I3, I4, I5, and I6 on an irregular grid.

In an exemplary embodiment of the invention, the points N1, N2 . . . $N_m$, mentioned above, do not have to be on a grid; however if a grid is not used other conditions may be required, for instance, that for each point its neighboring points are known. In particular the points N1, N2 . . . Nm may be nodes in a graph, as explained below. Alternatively, the neighboring points may be generated ad hoc.

In an exemplary embodiment of the invention the points N1, N2 . . . Nm which represent points in a physical space are organized as nodes in a graph. In optimization problems it is often possible to model various states of the system as discrete points in a state space. The discrete points of such a system can be represented by a "graph". The graph represents a physical system and comprising plural nodes and plural edges between respective nodes. Each node of the graph has a corresponding set of adjacent nodes. Each node of the graph is connected by an edge to another node and each edge has an associated cost. For example, if the system is a vehicle traveling between specified locations, then the state can be defined by a node in a graph, representing a geographical position of a vehicle. An estimated cost to target may be the Euclidian distance from the position to the target divided by the car speed. Unlike a general graph problem, however, in an exemplary embodiment of the invention, cost is defined for points that are not nodes and thus for edges that are not a priori defined.

In an exemplary embodiment of the invention there is no grid a-priori and the points N1, N2 . . . Nm, are determined as the path search progresses. For instance, choosing points based on selecting a radius from the starting point and/or selecting an angle. The method of selecting the points may be based, for example, on a local gradient in local cost. Alternatively, the selection may be randomized. This may be used, for example, in robotics where at any given time the robot has only a limited view (e.g., collecting information about other points may be expensive) and/or in order to get better approximations in areas with a high variance of local costs.

Several exemplary variations regarding cost are described. A "cost" associated with a path, for instance the accumulated path cost, can represent any quantifiable factor associated with the path and defined in terms of physical parameters of the system. For example, if the objective is to determine the shortest path over terrain and around obstacles, then cost represents the length of the path. If the objective is to minimize travel time of a car, then cost can represent the accumulated travel time over the path traveled. Further, it is well known that an optimization problem with objective (cost) function to be minimized generally can be reformulated as an equivalent problem with an objective (profit) function to be maximized.

In an exemplary embodiment of the invention not all neighbors of a point are involved in cost calculations. For instance, in the game example of FIG. 1, point S at coordinate 33 may have 8 neighbors at 22, 23, 24, 32, 35, 42, 43, 44, but only the 4 neighbors at 23, 32, 34, and 43 may be involved in cost calculations.

In some embodiments of the invention, when more neighbors of a point are used at 409 in FIG. 3A, a better approximation of accumulated path cost may be obtained.

In an exemplary embodiment of the invention neighbors don't have to be immediate (i.e. nearest) neighbors, but may be neighbors at a certain distance or radius from the point. Using a larger neighborhood may produce a better approximation of the ||gradient(U)|| mentioned above.

In an exemplary embodiment of the invention the neighborhood of a point is determined not by grid points or by points that are stored in the min-heap data structure. In one example, the cost of neighbors is calculated as an integral of a continuous cost function in a neighborhood of the point (if one is defined). In another embodiment, for example as defined above, neighbors may be selected randomly, according to areas of greater uncertainty in the wave-front propagation or according to cost of analyzing such neighbors. In some embodiments of the invention, the neighbors considered for cost are not the same as the neighbors considered for wave-front propagation.

In an exemplary embodiment of the invention computations can be done in parallel, for instance, the method can pull out all minimum total cost trial points together (if there is more than one) and do the update of the neighbors in parallel.

In an exemplary embodiment of the invention several target points may be considered for each starting point. A target point will be selected from several target points in advance or as the method proceeds using selection criteria. For instance, the method can select a target point that is estimated to result in a lower cost path.

In an exemplary embodiment of the invention several runs of the method are executed, different runs for different targets, and the target point for which a lower cost path was obtained is selected. The total run time may be much longer than if one target point was selected in advance.

The cost to target (H) from the current point to the target point is a feature of some embodiments of targeted marching. If the cost to target is underestimated, a more optimal path might be found, i.e. a path of less accumulated path cost, than if the cost to target is overestimated. However, an underestimated cost to target (H) may require targeted marching to examine more points or paths. Examining more points may result in a higher computational cost. Therefore it can be useful to overestimate the cost to target (H). In the game example the cost H can be underestimated by using a straight line (Euclidian distance or other physical-related distance) multiplied by the lowest possible local cost. A useful estimation can be taking an average path cost per unit length multiplied by the Euclidian distance from the point to the target. This is usually an underestimation, and only rarely an overestimation.

It should be noted that the various cost components need not all be calculated at a same time. In particular, it is noted that the estimated cost to target may be used as a method of applying a trade-off between time and optimality, by rejecting (or delaying) points which have a lower (apparent) probability of being useful. In one example, the cost at a point is calculated every cycle and the estimated cost to target is only calculated every few (e.g., 2, 3, 4, 5 or greater or fewer number) cycles (point selections), to assist in rejection such points. Other point rejection (or delaying) methods may be used in addition or instead, for example, cost based on curvature of the path so far or projected future curvature.

In an exemplary embodiment of the invention, points are not directly rejected. Instead, further exploration of points that look less promising is put off. Once a better path is found, these points are never related to. In an exemplary embodiment of the invention, the percentage of points not considered (in a regular grid, on a square of which the start and end points are opposite corners) is at least 30%, 50%, 60%, 70% or a greater or intermediate number. The application of the estimated cost to target, even if not applied every cycle, will cause the exploration of less desirable points to be put off, possibly indefinitely.

Targeted marching is optionally performed by a computerized system. Input to the system may be provided on a removable storage medium such as a CD-ROM, and/or using input devices, such as keyboard, and/or being transmitted by communication lines and/or by wireless communication. Input to the system can be provided by a user and/or by a device, for instance, a medical apparatus. Output of the system may be provided on a display and/or other output devices. In some cases, the output comprises carrying out of an action (e.g., travel) along the determined path. The system itself may comprise, for example, a memory for program and/or data and processing circuitry, for example a CPU. A non-volatile storage may also be provided. In general, a wide range of means for carrying out the methods and acts described herein will occur to a person skilled in the art and are considered (when suitably configured, arranged, manufactured and/or programmed), to be within the scope of the invention.

Vessel Centerline Example

In this example the method is applied to medical image data sets obtained, for example, from CT images. The method finds a path or a centerline within the volume of blood vessels or other lumens in a body, based on two or more points provided in the vessel. In an exemplary embodiment of the invention, "alive" points are not reinserted into to the min-heap. As the estimated cost to target is a continuous function, and optionally smooth, and the penalty for not re-inserting points may be small, this may assist in accelerating the centerline finding.

In this example there may be several points (e.g., at different locations along the blood vessel) that need to be connected and form a path from the beginning of the vessel to its end. In particular, those points are ordered and each said point needs to be connected to the one preceding it (if exist) and to the one following it (if exist).

In an exemplary embodiment of the invention, a wave-front is propagated simultaneously both from staring point S, and from target point T. Both waveforms meet at a meeting point. The generated path will be the concatenation of the path from the start point to the meeting point, and the path from the meeting point to the end point. Optionally, it is assumed that the two concatenated paths do not cross. In this embodiment of the invention additional bookkeeping (e.g., labeling) is optionally used. Labeling can be used, for example, to keep track of the origin (starting point) of a point on the wave-front. Optionally, such labeling is used to determine that a propagated wave-front does not propagate too far from and/or in a manner not generally parallel to the path connecting the start and end points. More details of a method of vessel centerline determination are described in a provisional application No. 60/536,661 entitled "Vessel Centerline Determination", filed on Jan. 15, 2004 and in a PCT application PCT/IL2004/001169 entitled "Vessel Centerline Determination", being filed on same date in the Israel Patent Office, the disclosures of which are incorporated herein by reference.

Robot Path Planning Example

A problem in robotic path planning is to find the shortest path for a robot taking into account constraints such as obstacles. Optionally, the robot is not merely a point in space, but its actual dimensions are considered.

Targeted marching may be used to solve the above robot path planning problem. Local cost (at 422) may be infinite at places that are closer to obstacles than the size of the robot, and may decline rapidly as the robot moves away from the obstacle. This is to allow the robot to move close to an obstacle, but keep a safe distance. Supposing that there is provided a circular robot of radius r, the center of the robot at point p, the distance d from the center of the robot to the nearest obstacle, and a safe distance s where s>r. The following local cost may be used:

if ($d<=r$) then local_cost=infinity;

if ($r<d<=s$) then local_cost=$1+1/(d-r)-1/(s-r)$;

if ($d>s$) then local_cost=1.

The cost to target (step 426) may be estimated as in the game example, for instance, as the Euclidian distance times the minimal local cost. However, better estimations can be calculated taking into consideration obstacles along the straight line between the point and the target, for example, associating such obstacles with a cost approximating a detour.

Image Transformation Example

In this example, it is desirable to determine the similarity of two images and the cost (e.g., number of steps) of changing from one image to another. A path is defined as a series of transformations that transform one image into another, such that the intermediate images are similar to each other. In the example of human faces, it is generally desirable that the intermediate images look like faces. This may also be useful, for example, in determining a similarity between a provided image and an image in a database (e.g., face or fingerprint data set). A grid of points (nodes) is given, wherein each point (node) in the grid represents a two dimensional (2D) image. Two neighbor images along a dimension of the grid vary by an image transformation. For instance, one dimension may represent skewing, another dimension may represent lighting, and another may represent blurring. Multiple (e.g., 3 or more) dimensions may be provided. A local cost of a point (node) in the grid is, for example, a number that indicates the similarity of the image the node represents to another certain known image type (e.g. a human face). The accumulated path cost of a point, is, for example, the similarity of the image represented by the point to the image at the starting point.

The determined path (if any) describes a series of image transformations from the image at the starting point S to the image at the target point T, where the images along the path found are similar to a certain known image type (e.g., a human face). For other image types, other transformations and transformation range values may be defined. In some cases, the limitations on the transformation are found by experimentation.

Object Stability Example

As a variation of the above "Image Similarity Example", each grid point represents an object rather than a 2D image, and the transformations are object deformations. Each object has an associated degree of instability or stability. It is desired to transform one object to another neighbor object, while minimizing the risk of the object falling apart. A possible local cost is the minus log probability that an object will remain stable. A possible accumulated path cost in this example represents the minus log probability that the entire transition from the initial state to the final state is successful.

General

While it is generally desirable to obtain an optimal solution, as noted above, such an optimal solution may not be searched for, instead, a cost-effective non-optimal solution may be sufficient. In an exemplary embodiment of the invention, the optimization function used is sub-optima. Alternatively or additionally, the approximation of an optimization function is sub-optimal. In an exemplary embodiment of the invention, the result is optimal to within 20%, 10%, 5%, 3% or better or an intermediate value. Optionally, an estimation of the lack of optimality is determined by executing the method multiple times with various parameters. A tradeoff between the best result and the cost of finding such a result may be factored into the execution of the method.

The present invention has been described using non-limiting detailed descriptions of embodiments thereof that are provided by way of example and are not intended to limit the scope of the invention. It should be understood that features described with respect to one embodiment may be used with other embodiments and that not all embodiments of the invention have all of the features shown in a particular figure or described with respect to one of the embodiments. It is noted that some of the above described embodiments may describe the best mode contemplated by the inventors and therefore include structure, acts or details of structures and acts that may not be essential to the invention and which are described as examples.

While targeted marching has been described as methods, it is meant to also encompass apparatus for carrying out the invention. The apparatus may be a system comprising of hardware and software. The apparatus may be a system, such as, programmed computers. The apparatus may include various computer readable media having suitable software thereon, for example, diskettes and computer RAM.

Structure and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

The invention claimed is:

1. A method of finding a path from a start point to a target point, in a physical space, wherein a substantially infinite number of paths exist in the space between the start point and the target point, the method comprising:

(a) selecting a plurality of points in the physical space from among the points comprised in said substantially infinite number of possible paths;

(b) computing, using a programmed general purpose computer and a cost function, a path cost from the start point to one of said plurality of points; said path cost representing an estimate of a minimal cost path from the start point to the one point which is acceptably accurate with respect to an optimization criterion;

(c) repeating (b) for a succession of others of said plurality of points to determine the path cost from the start point to each of said succession of other intermediate points;

d) computing estimated costs to target from the plurality of points for which path costs were determined in (b) and (c);

(e) selecting a group of points for further consideration according to those points determined in (b) and (c);

(f) repeating (b)-(e) to determine estimated total path costs to target for said selected group of points; and (g) after computing said costs, determining, using said computer, at least one of a minimal path or a minimal path cost of a path from the start point to the target point in the physical space, wherein the determination is based on said estimated total path costs and is an acceptably accurate estimate of the lowest cost path with respect to an optimization criterion.

2. A method according to claim 1, wherein selecting said plurality of points comprises generating a discrete model of said physical space.

3. A method according to claim 2, wherein the plurality of points and the selected group of points are on a regular grid.

4. A method according to claim 3, wherein said computing using a cost function comprises computing the cost function for grid points in a particular order.

5. A method according to claim 4, wherein selected group of points are neighbors of other points located at one or more adjacent grid points.

6. A method according to claim 5 wherein computing said path cost (u) at a point P, in a three dimensional grid, is carried out by solving the equation:

$$L^2 = \max(u - U_{x-1,y,z}, u - U_{x+1,y,z}, 0)^2 + \max(u - U_{x,y-1,z}, u - U_{x,y+1,z}, 0)^2 +$$

where L is the local cost and the U's are accumulated path costs for neighbors of P.

7. A method according to claim 2, wherein the points are arranged as a graph.

8. A method according to claim 5, wherein said points are on a grid, and are located at a certain distance or at a certain radius from the point.

9. A method according to claim 1, wherein the path cost at the target point approximates a minimal path cost of a path from the start point to the target point in the physical space.

10. A method according to claim 9, wherein the minimal path determined includes line segments which connect two of said group of selected points.

11. A method according to claim 10, wherein the minimal path cost has a lower or equal cost than any zigzag path from the start point to the target point, wherein the zigzag path connects a plurality of said points, only by straight line segments.

12. A method according to claim 1, wherein the minimal path determined is a continuous smooth line.

13. A method according to claim 1, comprising repeatedly updating the path costs until a stopping criteria is satisfied.

14. A method according to claim 13, wherein selecting said group of points for further consideration is done iteratively based on said computed path costs; and (f) is repeated for said iteratively selected points.

15. A method according to claim 14, wherein selecting said plurality of points comprises generating a discrete model of said physical space.

16. A method according to claim 13, wherein said estimated-cost-to-target computation is adjusted by deceasing the computed value for use in determination of the minimal path or minimal path cost.

17. A method according to claim 13, wherein said estimated cost to target computation is adjusted by increasing the computed value for use in determination of the minimal path or minimal path cost.

18. A method according to claim 13 wherein said estimated cost to target is based on a Euclidian distance to said target.

19. A method according to claim 13, wherein a collection data structure is used for obtaining a point with the smallest cost, wherein adding or removing a value from the collection, and reordering the collection has a computational cost of order O(log M) or better, where M is the number of points in the collection.

20. A method according to claim 19, wherein a heap-type data structure is used for obtaining a point with the smallest cost.

21. A method according to claim 13, wherein points are categorized and points of different categories are processed differently.

22. A method according claim 13, wherein costs of at least one point are updated after an initial calculation.

23. A method according to claim 13, wherein costs of no points are updated after an initial calculation.

24. A method according to claim 13, wherein the estimated cost-to-target computation is applied to less than all the points for which the path cost has been computed.

25. A method according to claim 13, wherein the estimated cost-to-target computation is applied first for the points for which the path cost is lowest.

26. A method according to claim 25, wherein said estimated cost-to-target computation is applied to 40% or less of the points for which the path cost has been computed.

27. A method according to claim 13, wherein use of said estimated cost to target minimizes computation time for a path that is an acceptable estimate of a minimum path cost from said start point to said target point.

28. A method according to claim 13, wherein the locations of said points are not limited by a set of predetermined alternative routes.

29. A method according to claim 13, wherein said total path cost is the calculated cost from the start point to the points comprised in said selected group of points plus the estimated cost from said intermediate point to said end point.

30. A method according to claim 13, wherein said path is determined from medical image data and represents a path or a centerline along a blood vessel or other lumen in a body.

31. A method according to claim 1, wherein the path cost of a point is a function of a local cost of the point and a calculated path cost of at least one neighbor point of the point.

32. A method according to claim 1, wherein computing said path costs comprises solving an Eikonal equation.

33. A method according to claim 32 wherein solving comprises employing a finite-difference approximation to an Eikonal equation.

34. A method according to claim 32 wherein computing said accumulated path cost at a point p is carried out by solving an Eikonal equation ||gradient(U(p))||=L(p), where U(p) is an accumulated path cost function, L(p) is a local cost function, || || is a norm, and where the condition L(p)>0 holds.

35. A method according to claim 1, wherein computing said path cost is carried out using cost calculations suitable for a fast marching method.

36. A method according to claim 1, wherein determining a path is carried out by a gradient descent method applied on said plurality of points and said selected group of points.

37. A method according to claim 36, wherein said gradient descent method is applied by:

(h) working backward from the target point to find a neighboring one of the selected group of points which has the lowest calculated cost;

(i) repeating (h) for points which are neighbors of the point determined in (h) to find the next lowest cost point;

(j) continuing iterations of (i) until a point is reached which has a total cost of zero; and (k) stopping the iteration of (i) and recognizing the point having a total cost of as the start point.

38. A method according to claim 1, wherein selecting said group of points for further consideration is done iteratively based on said computed path costs; and (f) is repeated for said iteratively selected points.

39. A method according to claim 12, wherein selecting said plurality of points comprises generating a discrete model of said physical space.

40. The method of claim 1, wherein the estimated total path costs to target is based on approximated total path cost for said selected group of points, where a total path cost is a function of the calculated costs from the start point to the points of said group of points and the estimated costs for said selected group of points to said target point.

41. The method of claim 40, wherein the path cost at the target point approximates a minimal path cost of a path from the start point to the target point in the physical space.

* * * * *

UNITED STATES PATENT AND TRADEMARK OFFICE

CERTIFICATE OF CORRECTION

PATENT NO. : 8,352,174 B2
APPLICATION NO. : 10/597221
DATED : January 8, 2013
INVENTOR(S) : Ido Milstein et al.

It is certified that error appears in the above-identified patent and that said Letters Patent is hereby corrected as shown below:

<u>The Invention claimed is:</u>

In claim 6, after " $\max\left(u-U_{x,y-1,z},u-U_{x,y+1,z},0\right)^2+$ "

insert -- $\max\left(u-U_{x,y,z-1},u-U_{x,y,z+1},0\right)^2$ --

In claim 39, line 1, change "12" to --13--

Signed and Sealed this
Fifteenth Day of October, 2013

Teresa Stanek Rea
*Deputy Director of the United States Patent and Trademark Office*

UNITED STATES PATENT AND TRADEMARK OFFICE

CERTIFICATE OF CORRECTION

PATENT NO. : 8,352,174 B2
APPLICATION NO. : 10/597221
DATED : January 8, 2013
INVENTOR(S) : Ido Milstein et al.

It is certified that error appears in the above-identified patent and that said Letters Patent is hereby corrected as shown below:

In the Claims:

Col. 17,

In claim 6, line 34, after " $\max\left(u - U_{x, y-1, z}, u - U_{x, y+1, z}, 0\right)^2 +$ "

insert -- $\max\left(u - U_{x, y, z-1}, u - U_{x, y, z+1}, 0\right)^2$ --

Col. 20,

In claim 39, line 1, change "12" to --13--

This certificate supersedes the Certificate of Correction issued October 15, 2013.

Signed and Sealed this
Twelfth Day of November, 2013

Teresa Stanek Rea
*Deputy Director of the United States Patent and Trademark Office*